US008003341B2

(12) United States Patent
Kuroda

(10) Patent No.: US 8,003,341 B2
(45) Date of Patent: *Aug. 23, 2011

(54) METHOD OF AMPLIFYING ATP AND USE THEREOF

(75) Inventor: Akio Kuroda, Hiroshima (JP)

(73) Assignee: Japan Science and Technology Agency, Kawaguchi-shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/769,100

(22) Filed: Apr. 28, 2010

(65) Prior Publication Data

US 2010/0311093 A1    Dec. 9, 2010

Related U.S. Application Data

(63) Continuation of application No. 10/566,957, filed as application No. PCT/JP2004/011186 on Jul. 27, 2004, now Pat. No. 7,745,160.

(30) Foreign Application Priority Data

Jul. 29, 2003   (JP) .................................. 2003-202992

(51) Int. Cl.
  *G01N 33/53*   (2006.01)
  *G01N 33/567*   (2006.01)
(52) U.S. Cl. ......... 435/7.91; 435/7.1; 435/7.21; 435/7.6
(58) Field of Classification Search .................. None
  See application file for complete search history.

(56) References Cited

U.S. PATENT DOCUMENTS

2003/0064394 A1   4/2003   Ohtake et al.

FOREIGN PATENT DOCUMENTS

| JP | 2001-299390 | 10/2001 |
| JP | 2002-530087 | 9/2002 |
| JP | 2002-543798 | 12/2002 |
| WO | 94/25619 | 11/1994 |
| WO | 98/48031 | 10/1998 |
| WO | 0029603 | 5/2000 |
| WO | 0068418 | 11/2000 |

OTHER PUBLICATIONS

ATP Bioluminescence Assay Kit CLS II product insert, version 3, Jul. 1999.*
Definition of kit from Oxford Dictionaries http://oxforddictionaries.com/search?q=kit&view=uk, retrieved Oct. 20, 2010.*
Kumar et al, Protein Folding and Function: The N-Terminal Fragment in Adenylate Kinase, Biophysical Journal, vol. 80, May 2001, pp. 2439-2454.
Tzeng et al, The Multiple Activities of Polyphosphate Kinase of *Escherichia coli* and Their Subunit Structure Determined by Radiation Target Analaysis, The Journal of Biological Chemistry, vol. 275, No. 6, Feb. 2000, pp. 3977-3983.
Bulow et al, Multienzyme Systems Obtained by Gene Fusion, Tibtech, Jul. 1991, vol. 9, pp. 226-231.
International Search Report for PCT/JP2004/011186 mailed on Sep. 7, 2004.
Ahn, et al. ATP, 2001, vol. 66, p. 647, Japan.
Brune, et al. Cloning and Sequencing of the Adenylate Kinase Gene (adk) of *Escherichia Coli*, Nucleic Acids Research, 1985, vol. 13, No. 19, pp. 7139-7151, England.
Akiyama, et al. The Polyphosphate Kinase Gene of *Escherichia Coli*, The Journal of Biological Chemistry, 1992, vol. 267, No. 31, pp. 22556-22561, USA.
Deluca, et al. Kinetics of the Firefly Luciferase Catalyzed Reactions, Biochemistry, vol. 13, pp. 921-925, 1974.
Bautista, et al. Adenosine Triphosphate Bioluminescence as a Method to Determine Microbial Levels in Scald and Chill Tanks at a Poultry Abattoir, Poultry Science, vol. 73, pp. 1673-1678, 1994.
Spencer, et al. Preparedness and Response to Bioterrorism, Journal of Infection, vol. 43, pp. 104-110, 2001.
Chittock, et al. Kinetic Aspects of ATP Amplification Reactions, Analytical Biochemistry, vol. 255, pp. 120-126, 1998.
Neuhard, et al. Purines and Pyrimidines, Biosynthesis and Conversions of Nucleotides, pp. 445-473, 1987.
Neidhardt. Chemical Composition and *Escherichia Coli*, Part I, Molecular Architecture and Assembly of Cell Parts, pp. 3-6, 1987.
Bert, et al. Multi-Resistant *Pseudomonas Aeruginosa* Outbreak Associated with Contaminated Tap Water in a Neurosurgery Intensive Care Unit, Journal of Hospital Infection, vol. 39, pp. 53-62, 1998.
Olsson, et al. Extraction and Determination of Adenosine 5'-Triphosphate in Bovine Milk by the Firefly Luciferase Assay, Biotechnology and Applied Biochemistry, vol. 8, pp. 361-369, 1986.
Shimomura, et al. Proceedings of Annual Conference of Society of Chemical Engineers, vol. 66, p. 647, 2001.
Satoh, et al. ATP Amplification for Ultrasensitive Bioluminescence Assay, Detection of a Single Bacterial Cell, Bioscience, Biotechnology, Biochemistry, vol. 68, pp. 1216-1220, 2004. Supplementary European Office Action for PCT/JP2004/011186 mailed on Jan. 29, 2008.
Chen, et al. Changing the Donor Cofactor of Bovine alpha 1,3-Galactosyltransferase by Fusion with UDP-galactose 4-Epimerase, Journal of Biological Chemistry, American Society of Biochemical Biologists, Oct. 2000, vol. 275, No. 41, pp. 31594-31600, Birmingham, US.
Meijer, et al. An Artificial Bifunctional Enzyme, gamma-Glutamyl Kinase/gamma-Glutamyl Phosphate Reductase, Improves NaCI Tolerance when Expressed in *Escherichia Coli*, Biotechnology Letters, 1996, vol. 18, No. 10, pp. 1133-1138.
Brodelius, et al. Fusion of Farnesyldiphosphate Synthase and Epiaristolochene Synthase, a Sesquiterpene Cyclase Involved in Capsidiol Biosynthesis in *Nicotiana Tobacum*, European Journal of Biochemistry, Jul. 2002, vol. 269, No. 14, pp. 3570-3577, Berlin, Germany.
Resnick, et al. In Vitro ATP Regeneration from Polyphosphate and AMP by Polyphosphate: AMP Phosphotransferase and Adenylate Kinase from *Acinetobacter johnsonii* 210A, Applied and Environmental Microbiology, May 2000, vol. 66, No. 5, pp. 2045-2051.
Office Action for U.S. Appl. No. 10/566,957 mailed on Aug. 3, 2009.

* cited by examiner

*Primary Examiner* — Oluwatosin Ogunbiyi
(74) *Attorney, Agent, or Firm* — Turocy & Watson, LLP

(57) ABSTRACT

The ATP amplification method is a method for amplifying and detecting a very trace amount of exogenous ATP by allowing a fusion protein (PPK-ADK) of a polyphosphate kinase and an adenylate kinase, the fusion protein not containing ADP, to act on a mixture of ATP, AMP, and a polyphosphate compound. Also provided is an ultrasensitive ATP amplification method by which ATP at a single cell level can be amplified and detected, and an ultrasensitive microbial assay based on this ATP amplification method.

3 Claims, 2 Drawing Sheets

(a) In the absence of ATP $$AMP + PolyP_n \rightarrow X$$

(b) In the presence of ATP

ADK: adenylate kinase
PPK: polyphosphate kinase

SEQUENCE LISTING

<160> NUMBER OF SEQ ID NOS: 4

<210> SEQ ID NO 1
<211> LENGTH: 30
<212> TYPE: DNA
<213> ORGANISM: Artificial Sequence
<220> FEATURE:
<223> OTHER INFORMATION: ppk forward primer

<400> SEQUENCE: 1
ggatctagat gaataaaacg gagtaaaagt                                30

<210> SEQ ID NO 2
<211> LENGTH: 42
<212> TYPE: DNA
<213> ORGANISM: Artificial Sequence
<220> FEATURE:
<223> OTHER INFORMATION: ppk reverse primer

<400> SEQUENCE: 2
ggaggatccg ccgccgccgc cttcaggttg ttcgagtgat tt                  42

<210> SEQ ID NO 3
<211> LENGTH: 30
<212> TYPE: DNA
<213> ORGANISM: Artificial Sequence
<220> FEATURE:
<223> OTHER INFORMATION: adk forward primer

<400> SEQUENCE: 3
ggaggatcca tgcgtatcat tctgcttggc                                30

<210> SEQ ID NO 4
<211> LENGTH: 27
<212> TYPE: DNA
<213> ORGANISM: Artificial Sequence
<220> FEATURE:
<223> OTHER INFORMATION: adk reverse primer

<400> SEQUENCE: 4
ggaaagcttg ccgaggattt tttccag                                   27

METHOD OF AMPLIFYING ATP AND USE THEREOF

CROSS-REFERENCE TO RELATED APPLICATIONS

This is a Continuation of application Ser. No. 10/566,957 filed Jan. 27, 2006, now U.S. Pat. No. 7,745,160 B2 issued Jun. 29, 2010 which is a national stage application under 35 USC §371 of International Application No. PCT/JP2004/011186 filed Jul. 27, 2004, which claims the benefit of priority from Japanese Application No. 2003-202992 filed Jul. 29, 2003, all of which are hereby incorporated by reference.

TECHNICAL FIELD

The present invention relates to a method for amplifying ATP, a method for rapidly detecting the presence of a microorganism using the amplification method, and a kit for the detection method.

BACKGROUND ART

In the food industry, dairy industry, and other industries, methods for rapidly detecting microorganisms with high sensitivity are very important, for example, in the control of environmental microorganisms such as the detection of microorganisms at food manufacturing plants for prevention of food poisoning, and in the inspection for contamination of microorganisms in food products (e.g., dairy products such as milk). In conventional methods for detecting living cells using a nutrient medium, it takes several days until a living microorganism is counted.

For the detection of microorganisms as described above, a method of utilizing ATP present in all organisms has been examined. As a method for detecting ATP, a bioluminescence assay employing firefly luciferase has been known. This method is an established technique for measuring ATP (see DeLuca, M. and W. D. McElroy, "Kinetics of the firefly luciferase catalyzed reactions," Biochemistry, vol. 26. pp. 921-925 (1974)) and has been used as a rapid, hygiene monitoring (Bautista, D. A. et al., "Adenosine triphosphate bioluminescence as a method to determine microbial levels in scald and chill tanks at a poultry abattoir," Poult. Sci., vol. 73, pp. 1673-1678 (1994)). Furthermore, an ATP assay has recently been proposed as a technology for countering bioterrorism (Spencer, R. C. and N. F. Lightfoot, "Preparedness and response to bioterrorism," J. Infect., vol. 43, pp. 104-110 (2001)).

However, the conventional methods for assaying ATP have a detection limit (e.g., approximately $10^4$ E. coli colony-forming units (CFU)/assay). Such a sensitivity is not sensitive enough for industrial or practical applications.

A computer simulation has suggested that ATP amplification employing adenylate kinase (ADK) and pyruvate kinase (PVK) provides a possibility that a very low level of ATP can be detected without using a photometer having high sensitivity (Chittock, R. S. et al., "Kinetic aspects of ATP amplification reactions," Anal. Biochem, vol. 255, pp. 120-126 (1998)). However, this method has not been utilized in practice.

In order to assay a trace amount of ATP, a method for amplifying ATP has been proposed (Japanese Laid-Open Patent Publication No. 2001-299390). This method disclosed in Japanese Laid-Open Patent Publication No. 2001-299390 will be described with reference to FIG. 1. In FIG. 1, ADK refers to adenylate kinase, polyP refers to polyphosphate, and PPK refers to polyphosphate kinase. Hereinafter, these abbreviations sometimes are also used in the present specification. FIG. 1a shows that in the absence of ATP, ATP is not theoretically produced from AMP and polyphosphate. As shown in FIG. 1b, in the presence of ATP, ADK causes a transphosphorylation from ATP to AMP, which results in a production of two molecules of ADP (first reaction). The two molecules of ADP produced in this first reaction receive a phosphate group from polyphosphate by the action of PPK, resulting in a production of two molecules of ATP (second reaction). The two molecules of ATP produced in this second reaction are used again for the first reaction to produce four molecules of ADP, and these four molecules of ADP are then converted into four molecules of ATP by PPK.

In this manner, according to Japanese Laid-Open Patent Publication No. 2001-299390, excess amounts of AMP and polyphosphate are added to the reaction system to drive the ADK and PPK equilibrium toward the production of ADP (first reaction) and the production of ATP (second reaction), respectively. Then, by repeating a single reaction system including the first reaction and the second reaction n times, one molecule of ATP is amplified to $2^n$ molecules of ATP. Therefore, this method is an excellent method for amplifying ATP.

Although this method described in Japanese Laid-Open Patent Publication No. 2001-299390 is an excellent method in that the presence of cells can be detected with a higher level of sensitivity than conventionally achieved, it turned out that in this method, amplification of ATP in the absence of ATP, which does not occur in theory, is sometimes observed at a low level, and thus there is a problem in that this method does not have reliability for amplifying and detecting exogenous (externally added) ATP only. That is to say, there is a problem in that this method cannot reliably provide such a sensitivity that ATP at a single cell level can be amplified and detected. Furthermore, there are also problems such as the adjustment between the activities of ADK and PPK.

DISCLOSURE OF INVENTION

There is a demand for a method for efficiently amplifying exogenous ATP. In particular, there is a demand for a method for amplifying exogenous ATP only and a high-sensitive detection method by which the presence of a single cell can be detected using this amplification method.

The present invention was achieved in order to solve the foregoing problems. By the ATP amplification method of the present invention, a very trace amount of ATP can be detected, and furthermore, the presence of only a single cell can be detected.

The present invention provides a method for amplifying ATP, including allowing a fusion protein of a polyphosphate kinase and an adenylate kinase to act on a mixture containing ATP, AMP, and a polyphosphate compound.

In a preferred embodiment, the fusion protein of a polyphosphate kinase and an adenylate kinase is a fusion protein that does not contain ADP.

Moreover, the present invention provides a method for detecting ATP, including allowing a fusion protein of a polyphosphate kinase and an adenylate kinase to act on a mixture of ATP, AMP, and a polyphosphate compound to amplify ATP; and detecting the amplified ATP.

In a preferred embodiment, the fusion protein of a polyphosphate kinase and an adenylate kinase is a fusion protein that does not contain ADP.

Furthermore, the present invention provides a method for rapidly detecting the presence of a microorganism, including treating a sample containing a microorganism to prepare a sample containing ATP; adding the sample containing ATP to an ATP amplification system to amplify ATP; and detecting the amplified ATP, wherein the ATP amplification system includes AMP, a polyphosphate compound, and a fusion protein of a polyphosphate kinase and an adenylate kinase, the fusion protein not containing ADP.

Moreover, the present invention provides a kit for rapidly detecting the presence of a microorganism, including an ATP amplification reagent containing AMP, a polyphosphate compound, and a fusion protein of a polyphosphate kinase and an adenylate kinase, the fusion protein not containing ADP; and an ATP detection reagent for detecting ATP.

In a preferred embodiment, the kit further includes a cell lysis reagent.

The present invention further provides a method for amplifying ATP by allowing an adenylate kinase and a polyphosphate kinase that does not contain ADP to act on a mixture of ATP, AMP, and a polyphosphate compound.

The present invention also provides a fusion protein of a polyphosphate kinase and an adenylate kinase, and a fusion protein of a polyphosphate kinase and an adenylate kinase, which does not contain ADP.

Figure 1:
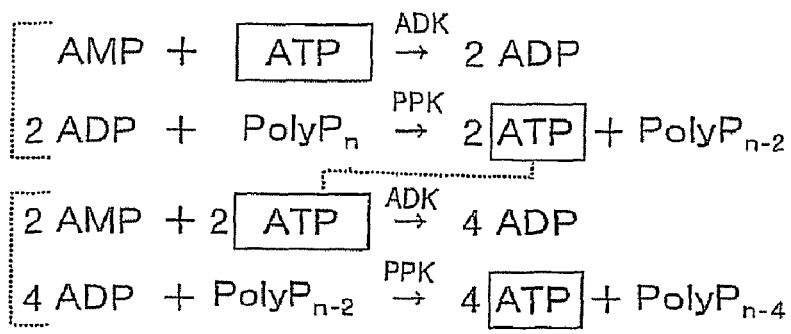
FIG. 1 is a schematic diagram showing an ATP amplification mechanism employing ADK and PPK.

BEST MODE FOR CARRYING OUT THE INVENTION (Fusion Protein)

Regarding the fusion protein of a polyphosphate kinase and an adenylate kinase (hereinafter sometimes referred to as the "PPK-ADK") that is used in the present invention, the order of a linkage of the enzymes is not particularly limited as long as the fusion protein reveals the PPK activity and ADK activity. The fusion protein preferably contains the PPK on the N-terminal side and the ADK on the C-terminal side. In this fusion protein, the PPK may be bound to the ADK directly or via a spacer. To purify the fusion protein, it is useful to attach a tag that does not affect the expression of the enzymes to the C-terminal of the fusion protein.

There is no particular limitation regarding the sources of a ppk gene encoding the PPK and an adk gene encoding the ADK, as long as the sequences of these genes are identified. The sequences of E. coli are preferably used.

By preparing appropriate primers based on these gene sequences and performing PCR, respective gene sequences can be obtained.

As a suitable primer for preparing the ppk gene, for example, a combination of the following primers is preferable: (1) a primer having a sequence for introducing an appropriate restriction enzyme recognition site upstream of the 5' end of the ppk gene; and (2) a primer having a spacer (e.g., glycine) sequence and a sequence for introducing an appropriate restriction enzyme recognition site in the spacer site or downstream thereof. When PCR is performed by using a combination of these two primers, a fragment containing a ppk gene that expresses a PPK having a spacer at the C-terminal is collected easily.

As a suitable primer for preparing the adk gene, the following primers are preferable as in the case of the ppk gene: (1) a primer having a sequence for introducing an appropriate restriction enzyme recognition sequence upstream of the 5' end of the adk gene; and (2) a primer having a C-terminal tag (e.g., histidine) sequence and having a sequence for introducing an appropriate restriction enzyme recognition sequence downstream of the C-terminal tag. When PCR is performed using a combination of these two primers, a fragment containing an adk gene that expresses an ADK having a tag at the C-terminal is collected easily.

Restriction enzymes of the above-described primers can be determined in view of the gene sequence of ppk or adk and a cloning site of a vector into which fragments are to be incorporated.

PCR is performed using the chromosomal DNA of E. coli as a template and the above-described primers, and the obtained DNA fragments are each cleaved with restriction enzymes to collect a fragment containing the ppk gene and a fragment containing the adk gene. The obtained fragments containing the respective genes are inserted into an appropriate vector so as to be arranged in order of ppk-adk, and thus a recombination vector that expresses a fusion protein of PPK-ADK can be obtained.

The obtained vector is introduced into an appropriate host (e.g., E. coli) to express the recombinant vector, and thus the PPK-ADK fusion protein is produced. The fusion protein designed to have a histidine tag (His-tag) is purified and collected easily by using a Hitrap chelating column.

The obtained fusion protein, PPK-ADK, can be used for an ATP amplification without being subjected to any treatment. However, as discussed below, it turned out to be improper to measure exogenous ATP. This may be because ADP is present as bound to PPK. The ADP bound to PPK may serve as a substrate of the PPK in the presence of a polyphosphate compound, and this ADP may be converted into ATP by PPK. That is to say, it seems that in a reaction system as shown in FIG. 1, a reaction from ADP to ATP, which is the second reaction, occurs first even in the absence of ATP, and this ATP is then used in the first reaction, thereby initiating an ATP amplification automatically. Therefore, in order to measure exogenous ATP only, it is necessary to remove the ADP bound to the PPK in advance.

Removal of the ADP, which is an impurity bound to PPK, is performed by an apyrase treatment, for example. Apyrase removes a phosphate group from ATP or ADP to produce AMP. The apyrase treatment is preferably performed in the presence of an appropriate amount of pyrophosphate. Pyrophosphate promotes release of the ADP bound to PPK-ADK, so that the ADP becomes susceptible to attack by apyrase. The apyrase-treated PPK-ADK is collected using a Hitrap chelating column again. The collected PPK-ADK retains the respective activities (i.e., PPK activity and ADK activity) even after the apyrase treatment.

(Amplification of ATP Using PPK-ADK)

The amplification of ATP using the PPK-ADK of the present invention is performed by allowing the PPK-ADK to act on ATP, an excess amount of AMP, and an excess amount of a polyphosphate compound. That is to say, it is performed by adding ATP to a mixture of AMP, the polyphosphate compound, and the PPK-ADK or by adding the PPK-ADK to a mixture of ATP, AMP, and the polyphosphate compound. The mode of the reaction is the same as in FIG. 1, and the first reaction and the second reaction shown in FIG. 1 are repeated to amplify ATP.

The amplification of ATP is performed in an appropriate buffer solution at an appropriate temperature (e.g., 30 to 40° C.) for an appropriate period of time (e.g., 5 minutes to 2 hours). When it seems that ATP is present in a trace amount, the amplification reaction is preferably performed for about one hour.

As the polyphosphate compound, polyphosphoric acid or a salt thereof is used. Preferably, a compound in which 10 to 1000, preferably 10 to 100 phosphate molecules are linearly polymerized is used advantageously. The polyphosphate may be derived from bacteria or may be chemically synthesized. Alternatively, it may be synthesized from ATP using a polyphosphate synthetase.

(Detection of ATP)

Regarding the method for detecting the amplified ATP, a method usually used by those skilled in the art can be employed, and there is no particular limitation. Generally, the detection is performed by measuring the amount of luminescence due to a reaction of a luciferase with ATP. For example, a commercially available ATP measurement kit employing luciferase can be used.

(Method for Rapidly Detecting the Presence of a Microorganism)

This method is a method in which, focusing on the fact that ATP is contained in the cells of all organisms, a sample containing ATP is prepared from a sample containing a microorganism, and ATP is amplified using the above-described ATP amplification method and detected. The use of the PPK-ADK subjected to the ADP removal treatment allows the measurement of exogenous ATP. For example, ATP contained in a single cell can be amplified to a measurable level, so that the presence of only one microorganism can be detected. Considering that the detection limit of the conventional methods was $10^4$ colony-forming units (CFU) of $E.$ $coli$ per assay, the detection sensitivity is increased by a factor of at least 10,000.

It should be noted that the microorganism contains ADP. When the PPK-ADK subjected to the ADP removal treatment is used, when ADP is added to the amplification system of the present invention, the ADP is converted into ATP, and thus an ATP amplification is initiated. Therefore, the amplification method of the present invention is superior in that even when ATP is degraded into ADP during a pre-treatment for the detection of a microorganism, the sensitivity in the present invention is not affected. Hereinafter, in the context of the detection of a microorganism, a sample of ATP to be measured is meant to include a case where ADP is contained in the sample.

There is no particular limitation regarding the method for preparing an ATP-containing sample from a microorganism-containing sample. It is possible to lyse a cell, but in view of influences of enzymes such as PPK and ADK contained in that cell, a method of performing a heat treatment to elute ATP or a method of lysing the cell, eluting ATP, and then performing a heat treatment for inactivating the other enzymes is most preferably employed. The heat treatment is performed, for example, at 100° C. for 1 to 5 minutes. The cell lysis treatment can be performed using a lysis buffer, e.g., a lysis buffer that is included with a commercially available ATP assay kit.

Such a sample that is obtained by performing the ATP release treatment and that seems to contain ATP is added to a mixture of AMP, the polyphosphate compound, and the PPK-ADK to perform an ATP amplification, and then the presence of ATP is detected using, for example, an ATP detection method employing luciferase. If ATP is contained in the sample, then it reacts with the luciferase and luminescence is observed. It should be noted that since ATP is amplified, a luminometer having high sensitivity is not necessarily required.

The present invention also provides a kit for rapidly detecting the presence of such a microorganism. That is to say, a kit including an ATP amplification reagent containing AMP, polyphosphate, and a PPK-ADK that does not contain ADP and an ATP detection reagent for detecting ATP is provided. This kit may further include a cell lysis reagent. The composition of the cell lysis reagent may be changed depending on the cells to be detected (e.g., a microorganism, a somatic cell, and the like).

The presence of a microorganism can be detected rapidly by subjecting a sample that seems to contain the microorganism to a heat treatment, adding the sample to the ATP amplification reagent of this kit to perform an amplification for an appropriate period of time, and then confirming the presence of ATP with the ATP detection reagent. This method was accomplished by use of PPK-ADK obtained by performing the ADP removal treatment so as to detect exogenous ATP. As the ATP detection reagent, a reagent using a luciferase-luciferin reaction system is commonly used, and the term "ATP detection reagent" used herein conceptually includes also a bioluminescence (fluorescence) measuring instrument.

(ATP Amplification Using ADK and PPK that does not Contain ADP)

The present invention also provides a method for amplifying ATP by allowing an ADK and a PPK that does not contain ADP to act on a mixture containing ATP, AMP, and polyphosphate. The PPK that does not contain ADP is prepared, for example, in the same manner as in the preparation of the fusion protein described above. In brief, a DNA fragment containing a ppk gene that expresses a PPK having a His-tag is collected using a primer having an appropriate restriction enzyme recognition sequence upstream of the 5' end of the ppk gene and a primer having a His-tag sequence and having an appropriate restriction enzyme recognition sequence downstream thereof. The obtained DNA is introduced into an appropriate vector to obtain a recombinant plasmid, which is then introduced into $E.$ $coli$ to express the PPK. The PPK is purified by using a Hitrap chelating column, treated with apyrase in the presence of pyrophosphate, and subjected to a Hitrap chelating column again to collect the PPK from which ADP has been removed. By using this PPK in the reaction system shown in FIG. 1, a method for amplifying and detecting exogenous ATP only is provided.

EXAMPLES

Hereinafter, the present invention will be described by means of examples, but the present invention is not limited to these examples.

In the examples, AMP and ATP used were purchased from Wako Pure Chemical Industries, Ltd. (Osaka) and Sigma, respectively. The AMP was further purified by using a TSK-gel SAX column (TOSOH) with 0.2 M KCl and 1% EDTA (pH 10) as a solvent. As the polyphosphate, polyphosphate having an average chain-length of 65 (Sigma) was used. A bioluminescence assay kit (CLSII) including luciferin and luciferase was purchased from Roche. Apyrase was purchased from Sigma.

Example 1

Preparation of PPK-ADK

Primers for obtaining a gene (ppk) encoding $E.$ $coli$ polyphosphate kinase (see Akiyama, M. et al., "The polyphosphate kinase gene of *Escherichia coli*. Isolation and sequence of the ppk gene and membrane location of the protein," J. Biol. Chem., vol. 267, pp. 22556-22561 (1992)) are as follows:

GGATCTAGATGAATAAAACGGAGTAAAAGT        (SEQ ID No: 1)
and

GGAGGATCCGCCGCCGCCGCCTTCAGGTTGTTCGAGTGATTT.    (SEQ ID No: 2)

The primer of SEQ ID No 1 has a sequence for introducing a restriction enzyme XbaI recognition site in the 5' terminal of the ppk gene. SEQ ID No: 2 is designed so that four glycines are attached to the C-terminal of the PPK, and further has a sequence for introducing a restriction enzyme BamHI recognition site in the 3' terminal.

Primers for obtaining a gene (adk) encoding *E. coli* adenylate kinase gene (Brune, M. et al., "Cloning and sequencing of the adenylate kinase gene (adk) of *Escherichia coli*," Nucleic Acids Res., vol. 13, pp. 7139-7151 (1985)) are as follows:

GGAGGATCCATGCGTATCATTCTGCTTGGC    (SEQ ID No: 3)
and

GGAAAGCTTGCCGAGGATTTTTTCCAG.    (SEQ ID No: 4)

The primer of SEQ ID No: 3 has a sequence for introducing a restriction enzyme BamHI recognition site in the 5' terminal of the adk gene. The primer of SEQ ID No: 4 is designed so that histidine, which is a C-terminal tag, is attached to the C-terminal of the ADK, and further has a sequence for introducing a restriction enzyme HindIII recognition site in the 3' terminal.

PCR was performed in the commonly used manner by using the chromosomal DNA of *E. coli* as a template and the above-described primers to obtain DNA fragments containing the ppk gene and the adk gene, respectively. The obtained DNA fragment containing the ppk gene was inserted into a pGEMT vector (Promega) to obtain a pGEMTppk. The obtained DNA fragment containing the adk gene was inserted into a pGEMT vector (Promega) to obtain a pGEMTadk.

A 2.1 kb fragment obtained by digesting the pGEMTppk with XbaI-BamHI and a 0.6 kb fragment obtained by digesting the pGEMTadk with BamHI-HindIII were ligated to a XbaI-HindIII digest of a pET vector (Stratagene), thereby constructing a plasmid pETppkadk. This plasmid contains a gene encoding a fusion protein of PPK and ADK with C-terminal His-tag in which PPK is bound to ADK via the four glycines.

This plasmid pETppkadk was introduced into *E. coli* (*E. coli* BL21), and the resultant transformant was cultured for 2 hours, and then 1 mM IPTG was added to a growth medium. After 4 hours of incubation, the transformant was harvested by centrifugation and suspended in a 20 mM phosphate buffer (pH 7) containing 0.5 M NaCl. The cells were lysed with a B-PER reagent (Pierce) and then treated with DNase and RNase in the presence of 1 mM PMSF. The supernatant was obtained by centrifugation, filtrated through a 0.2 μm filter, and then loaded onto a Hitrap chelating column (Amersham Bioscience). The column was washed with 0.1 M pyrophosphate, 20 mM phosphate, 0.5 M NaCl, 50 mM imidazole, and 20% glycerol (pH 7.4). A PPK-ADK fusion protein was eluted with 0.1 M pyrophosphate, 20 mM phosphate, 0.5 M NaCl, 0.5 M imidazole, and 20% glycerol (pH 7.4).

The obtained PPK-ADK fusion protein had the activities of ADK (43 U/mg) and PPK (38 U/mg) and produced ATP from AMP and polyphosphate. It should be noted that one unit of PPK synthesizes 1.0 μmol/minute of ATP from ADP and polyphosphate at 37° C. One unit of ADK synthesizes 1.0 μmol/minute of ATP from ADP at 37° C.

Then, 50 μl of a reaction mixture containing 0.16 μg of the PPK-ADK, 10 μM AMP, 400 μM polyphosphate, 8 mM $MgCl_2$, and 60 mM Tris-HCl (pH 7.4) were prepared. Then, 5 μl of the reaction mixture were sampled and mixed with 40 μl of the ATP bioluminescence assay reagent (Roche), and luminescence was measured immediately by using a multiplate luminometer (ARVO, Wallac).

Figure 2:
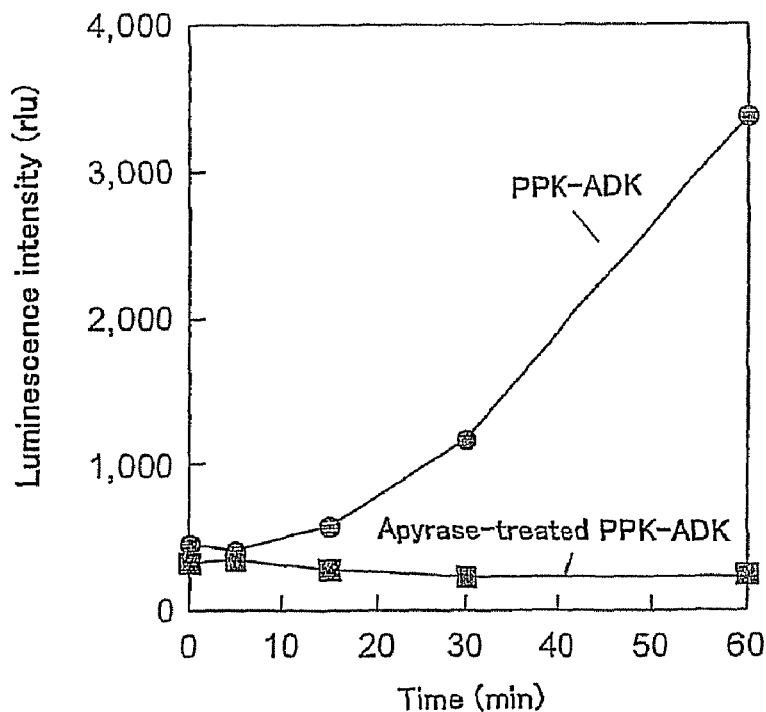
FIG. 2 is a graph showing the results of ATP amplifications employing a PPK-ADK and an apyrase-treated PPK-ADK.

As indicated by PPK-ADK in FIG. 2, amplification of ATP occurred in this reaction system that did not contain ATP, and luminescence was observed. The cause of this phenomenon was examined, and it was suggested that since ADP was bound to the PPK, this ADP was used by the PPK to firstly cause the second reaction shown in FIG. 1 to produce ATP and this ATP might then be amplified.

Example 2

Removal of ADP Bound to PPK-ADK

In order to remove the ADP, which was an impurity bound to the PPK-ADK obtained in Example 1, 180 μg of the PPK-ADK were reacted with apyrase (200 U) for one hour in the presence of 60 mM Tris-HCl (pH 8), 8 mM $MgCl_2$ and 10 mM polyphosphate. After the reaction was finished, the PPK-ADK from which the ADP was removed was collected by using a Hitrap chelating column again. Hereinafter, this PPK-ADK is referred to as the "apyrase-treated PPK-ADK". It should be noted that one unit of apyrase releases 1 μmol of phosphate from ATP or ADP per minute at 30° C.

Next, 50 μl of a reaction mixture containing 0.16 μg of the apyrase-treated PPK-ADK, 10 μM AMP, 400 μM polyphosphate, 8 mM $MgCl_2$, and 60 mM Tris-HCl (pH 7.4) were prepared. Then, 5 μl of the reaction mixture were sampled and mixed with 40 μl of an ATP bioluminescence assay reagent (Roche), and luminescence was measured immediately by using a multiplate luminometer (ARVO, Wallac).

As shown in FIG. 2, in the reaction using the apyrase-treated PPK-ADK, luminescence was not observed even after 60 minute reaction. It should be noted that although not shown in the drawing, when ATP was added to this mixture, luminescence was observed. From this fact, it was found that the apyrase treatment does not affect the ADK activity and the PPK activity of the PPK-ADK and that as a result of removing the impurity, ADP, by the apyrase treatment, ATP amplication did not occur when the endogenous ATP was not added into the reaction mixture. Accordingly, it is believed that the luminescence observed when ATP was added was caused purely by the exogenous ATP. Therefore, the apyrase-treated (ADP-free) PPK-ADK is very useful in assay of exogenous ATP.

It should be noted that, in the apyrase treatment, it is preferable to add pyrophosphate to a washing buffer and an elution buffer when the PPK-ADK is adsorbed on a Hitrap chelating column and eluted from the column. Since 0.1 M pyrophosphate has an effect of releasing ADP from the PPK-ADK, ADP can be removed more efficiently.

Example 3

Ultrasensitive Bioluminescence Assay

First, 48 μl of a reaction mixture containing 0.16 μg of the apyrase-treated PPK-ADK, 10 μM AMP, 400 μM polyphosphate, 8 mM $MgCl_2$ and 60 mM Tris-HCl (pH 7.4) were prepared, and then 2 μl of an ATP sample were added to this reaction mixture to amplify ATP. Thereafter, 5 μl of the reaction mixture were sampled over time and mixed with 40 μl of an ATP bioluminescence assay reagent, and luminescence was measured immediately by using a multiplate luminometer. For comparison, a sample was prepared without amplifying ATP (without adding the PPK-ADK), and the luminescence thereof was measured. Each value of luminescence is the mean±standard deviation of three different measurements. The increase in luminescence over time is shown in FIG. 3, and the results of ATP amplification after 60 minutes are shown in Table 1.

TABLE 1

| ATP (fmol) | Luminescence (rlu) ATP amplification | |
|---|---|---|
| | Without | With |
| 330 | 813 ± 22 | 28,180 ± 1606 |
| 33 | 113 ± 14 | 18,793 ± 241 |
| 3.3 | 50 ± 6 | 8,767 ± 443 |
| 0.33 | 52 ± 9 | 4,455 ± 36 |
| 0.033 | 53 ± 12 | 2,734 ± 233 |
| 0.0033 | 62 ± 12 | 1,553 ± 102 |
| 0 | 51 ± 2 | 229 ± 26 |

Figure 3:
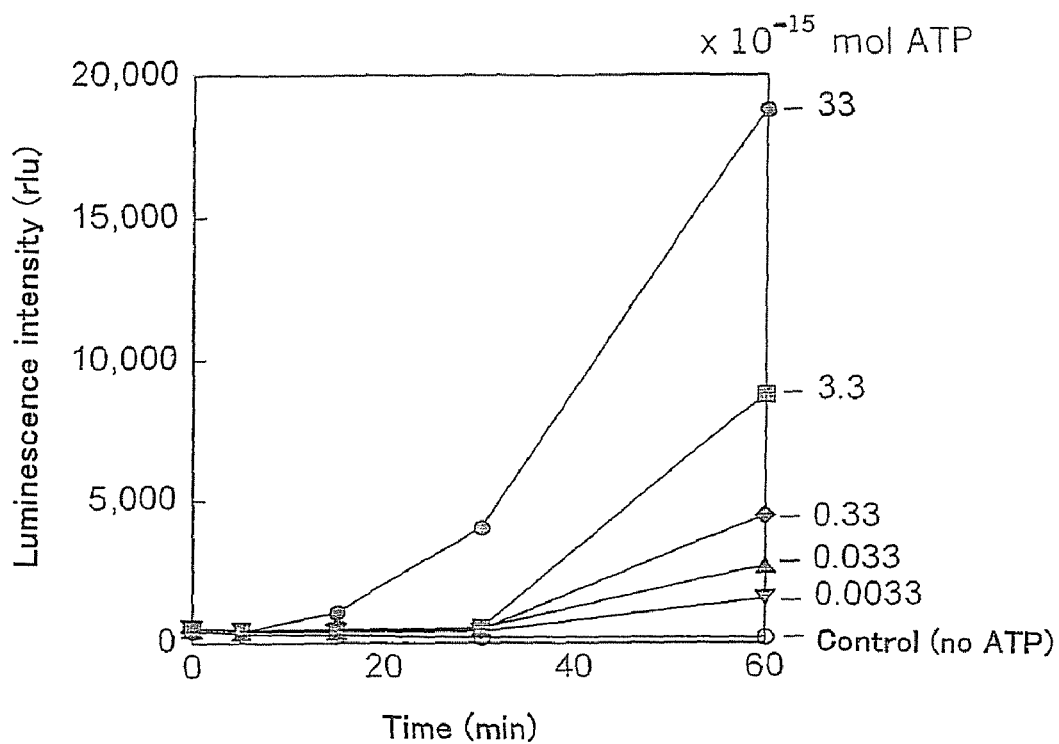
FIG. 3 is a graph showing the results of ATP amplifications performed on samples containing very trace amounts of ATP.

As shown in FIG. 3, it was found that when exogenous ATP was not present, the apyrase-treated PPK-ADK did not amplify ATP at all in spite of an amplification treatment for 60 minutes. Furthermore, as shown in FIG. 3 and Table 1, it was found that in spite of a low initial concentration of ATP, ATP can be amplified to such an extent that luminescence can be measured. The results show that this ATP amplification is applicable to an ultrasensitive bioluminescence assay. In other words, it was shown that by subjecting a sample containing ATP in a concentration of 0.0033 femtomoles (fmol: $10^{-15}$ mol=3.3 attomoles: $10^{-18}$ mol) to an ATP amplification treatment for 60 minutes, ATP can be amplified to a detectable level. That is to say, it became possible to detect ATP at a concentration of several attomoles (amol: $10^{-18}$ mol). On the other hand, conventional bioluminescence requires several tens femtomoles (fmol: $10^{-15}$ mol) of ATP to measure the luminescence thereof (Table 1). Thus, it is shown that by using the ATP amplification method of the present invention, the sensitivity of bioluminescence was increased by a factor of at least 10,000.

Example 4

Application of Ultrasensitive Bioluminescence Assay in Detecting a Single Microorganism The E. coli culture ($2 \times 10^9$ CFU/ml) was diluted to an appropriate concentration with pure water. The cell suspension (500 μl) was added to 500 μl of a lysis buffer (bioluminescence assay kit, Roche) and heated to 100° C. for 2 minutes to release ATP from the cells. Thereafter, 2 μl of the heated sample were subjected to an ATP amplification assay to measure bioluminescence.

For comparison, a sample was prepared without amplifying ATP (without adding the PPK-ADK), and the luminescence thereof was measured. Each value of luminescence is the mean±standard deviation of three different measurements. The increase in luminescence over time is shown in FIG. 4, and the results of ATP amplification after 60 minutes are shown in Table 2.

TABLE 2

| E. coli cells per assay (CFU) | Luminescence (rlu) ATP amplification | |
|---|---|---|
| | Without | With |
| 100,000 | 1,126 ± 255 | 39,722 ± 1,596 |
| 10,000 | 296 ± 34 | 33,903 ± 2,244 |
| 1,000 | 52 ± 4 | 16,901 ± 1890 |
| 100 | 37 ± 4 | 6,823 ± 205 |
| 10 | 39 ± 6 | 3,280 ± 604 |
| 1 | 37 ± 7 | 1,714 ± 44 |
| 0 | 43 ± 12 | 364 ± 73 |

Figure 4:
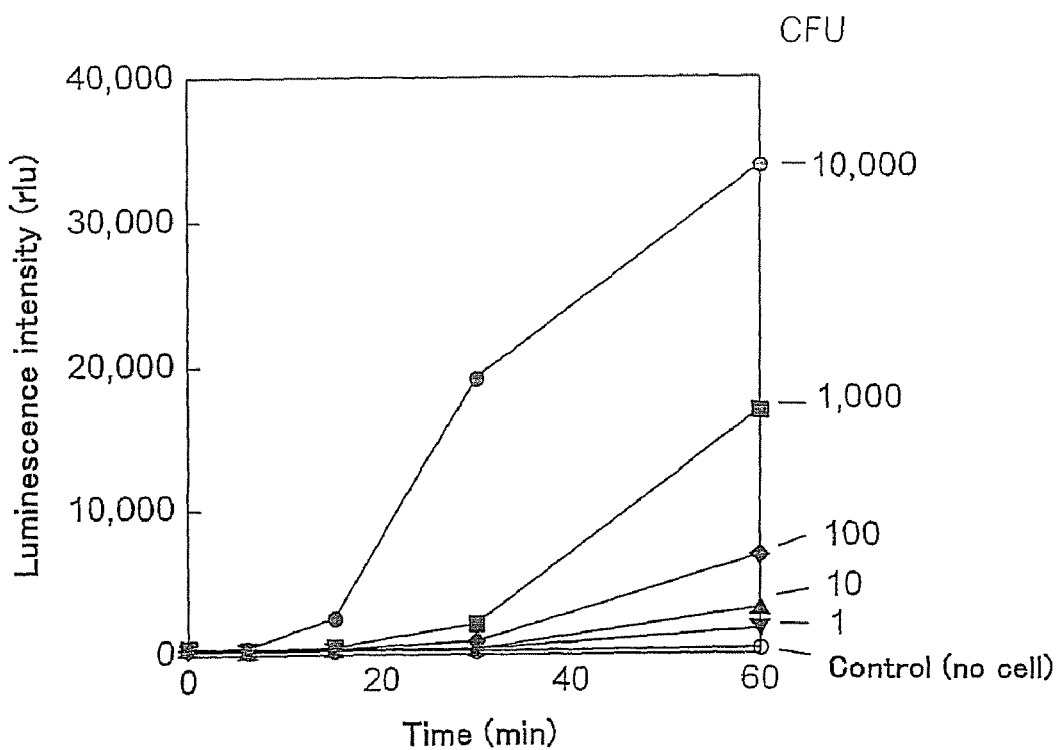
FIG. 4 is a graph showing the results of ATP amplifications performed on samples containing cells in predetermined concentrations.

As shown in Table 2 and FIG. 4, the amount of luminescence was varied depending on the number of E. coli cells used in the assay (FIG. 4). As shown in Table 2, when compared to the case where ATP amplification was not performed, the luminescent development was significantly enhanced in the case where ATP amplification was performed. Without ATP amplification, the degree of luminescent development was very low even in the case of 10,000 CFU in Table 2, and several 10,000 CFUs of E. coli cells were required to attain a significant level of bioluminescence. On the other hand, when the ATP amplification technique of the present invention was used, a distinct luminescence was observed even at the lowest level of a single E. coli cell (the level corresponding to 1 CFU of E. coli cell). This shows that the sensitivity was higher than in the case where ATP amplification was not performed by a factor of 10,000 or more.

It has been reported that the intracellular ATP level of the E. coli cells is about 7 μmol/g dry cells (Neuhard, J., and Y. Nygaard, "Purines and pyrimidines," pp. 445-473, F. C. Neidhardt et al. ed., "*Escherichia coli* and *Salmonella typhimurium*: cellular and molecular biology," ASM press, Washington, D.C. (1987)). Since the dry weight of one E. coli cell is about $2.8 \times 10^{-13}$ g (F. C. Neidhardt, "Chemical composition of *Escherichia coli*," pp. 3-6, F. C. Neidhardt et al. ed., "*Escherichia coli* and *Salmonella typhimurium*: cellular and molecular biology," ASM press, Washington, D.C. (1987)), E. coli contains about 2 attomoles of ATP per cell. This level of ATP is almost equal to that of the detection limit of this ultrasensitive bioluminescence assay.

Example 5

Application of Ultrasensitive Bioluminescence Assay to Hygiene Monitoring

The inventor of the present invention has examined whether or not the method of the present invention is applicable to swab monitoring of E. coli. First, a cell suspension of E. coli was spread on a polystyrene petri dish, air-dried, and swabbed with a commercially available cotton swab. Since the commercially available cotton swab contains a significant amount of ATP, it was previously autoclaved at 121° C. for 75 minutes to decompose ATP to AMP and phosphate. The sample swabbed from a surface area of 4 $cm^2$ was dipped into 400 μl of a lysis buffer, and then heated at 100° C. for 2 minutes. The heated sample (10 μl) was added to an ATP amplification reaction solution (40 µl), and an ATP amplification reaction was performed for 60 minutes. Then, 25 µl of the reaction mixture were used for a bioluminescence assay. The results are shown in Table 3.

TABLE 3

| Number of E. coli cells | Luminescence (rlu) ATP amplification | |
|---|---|---|
| (CFU) | Without | With |
| 120,000 | 223 | 30,630 |
| 2,000 | 62 | 23,835 |
| 1,200 | 52 | 10,215 |
| 120 | 51 | 2,685 |
| 12 | 53 | 1,653 |
| 0 | 65 | 404 |

By this swab monitoring, a measurement at a level of about 12 CFU of E. coli/cm$^2$ was possible. It was found that the method of the present invention is applicable to swab monitoring of E. coli.

Example 6

Detection of Bacteria in Drinking Water

The inventor of the present invention has examined whether or not the method of the present invention is effective in detecting bacteria in drinking water. First, a water sample (2 µl) heated was added to an ATP amplification reaction solution (50 µl), and an ATP amplification was performed for 60 minutes. The results are shown in Table 4. In Table 4, "tap water (1)" was obtained from a water supply in Hiroshima city. "Tap water (2)" is a water recycled in the Hiroshima University. "Bottled water" was purchased commercially. "Sterilized water" was prepared by autoclaving distilled water. "Pond water" is the water of a pond at the Hiroshima University. The number of colonies (CFU) was obtained by applying 1 ml of a water sample on a nutrient agar medium (1.6 g of tryptone, 1 g of yeast extract, 0.5 g of NaCl, 15 g of agar, and 1 L of water) and counting the colonies formed after 3 days of cultivation at 28° C.

TABLE 4

| Sample source | Luminescence (rlu) ATP amplification | | Number of colonies |
|---|---|---|---|
| | Without | With | (CFU) |
| Tap water (1) | 15 | 1,400 | 33 |
| Tap water (2) | 13 | 413 | 1 |
| Bottled water | 30 | 239 | >1 |
| Sterilized water | 23 | 254 | >1 |
| Pond water | 9 | 3100 | 59 |

The results indicate that bacteria could be detected even at a level at which they cannot be detected by the conventional bioluminescence assays. As shown by the results in Table 4, it is found that it is possible to detect 1 CFU/ml of bacteria by subjecting the water samples to an ATP amplification treatment for 60 minutes by using the method of the present invention. The conventional method using a nutrient medium typically requires several days to detect bacterial contamination (Table 4). It has been reported that Pseudomonas aeruginosa, which is a pathogenic bacterium, was detected in tap water (Bert, F. et al., "Multi-resistant Pseudomonas aeruginosa outbreak associated with contaminated tap water in a neurosurgery intensive care unit," J. Hosp. Infect., vol. 39, pp. 53-62 (1998)), and the presence of such a microorganism can be detected easily and rapidly according to the present invention.

Example 7

Detection of Bacteria in Milk

The application in dairying was examined. Since bacterial contamination causes extensive damage in the milk industry, rapid and reliable tests for detecting bacteria in milk have been developed. The inventor of the present invention further examined a high-sensitive assay for detecting Staphylococcus aureus in milk. A growth culture of Staphylococcus aureus was diluted to an appropriate concentration and added to milk. In order to remove non-bacterial ATP derived from mammary gland and somatic cells that is contained in milk, 0.5 ml of milk were filtrated through a 0.45 µm membrane filter. This membrane filter was washed with 10 ml of a solution containing 0.2% Triton X-100, 100 mM Tris-HCl (pH 7.8), and 2 mM EDTA (Olsson, T. et al., "Extraction and determination of adenosine 5'-triphosphate in bovine milk by the firefly luciferase assay. Biotech," Appl. Biochem, vol. 8, pp. 361-369 (1986)). After washing, this membrane filter was dipped into 200 µl of a lysis buffer, and heated to 100° C. for 5 minutes. The heated sample (20 µl) was subjected to an ATP amplification for 60 minutes. Then, the sample was used for a bioluminescence assay. The results are shown in Table 5.

TABLE 5

| Number of S. aureus cells (CFU)/ | Luminescence (rlu) ATP amplification | |
|---|---|---|
| 0.5 ml milk | Without | With |
| 750,000 | 399 | 39,491 |
| 75,000 | 84 | 10,011 |
| 7,500 | 47 | 4,141 |
| 750 | 50 | 1,790 |
| 75 | 37 | 1,156 |
| 0 | 49 | 432 |

As a result of the assay, 75 CFU (Staphylococcus aureus)/0.5 ml milk could be detected. Although the sensitivity in the detection of Staphylococcus aureus was lower than that of E. coli, the sensitivity in the detection of Staphylococcus aureus in milk was enhanced to about 10,000 times higher than that of a conventional bioluminescence assay. The method for rapidly determining the presence of a microorganism of the present invention is applicable to not only microorganisms in the environment but also a wide range of hygiene monitoring techniques.

INDUSTRIAL APPLICABILITY

The PPK-ADK fusion protein of the present invention acts on a mixture of ATP, AMP, and a polyphosphate compound to amplify ATP. In particular, by using a PPK-ADK that does not contain ADP, which is an impurity, it becomes possible to amplify exogenous ATP, so that ATP derived from a microorganism at a single cell level can be amplified. The amplified ATP can be detected by a luciferase assay, for example. Therefore, a microorganism, detection of which has conventionally taken at least several days, can be detected very rapidly, and furthermore, even only a single cell can be detected.

What is claimed is:

1. A kit for detecting the presence of a microorganism, comprising an adenosine triphosphate amplification reagent containing adenosine monophosphate, a polyphosphate compound, and a fusion protein that has a polyphosphate kinase and an adenylate kinase in this order from the N-terminal; and an adenosine triphosphate detection reagent for detecting adenosine triphosphate, wherein the fusion protein has been subjected to an apyrase treatment and a pyrophosphate treatment so as to remove adenosine diphosphate bound to the fusion protein and wherein the fusion protein is not present in a complex with adenosine diphosphate.

2. The kit of claim 1, further comprising a cell lysis reagent.

3. A fusion protein that has a polyphosphate kinase and an adenylate kinase in this order from the N-terminal and that has been subjected to an apyrase treatment and a pyrophosphate treatment so as to remove adenosine diphosphate bound to the fusion protein, wherein the fusion protein is not present in a complex with adenosine diphosphate.

* * * * *